United States Patent [19]

Hegde et al.

[11] Patent Number: 5,342,852
[45] Date of Patent: Aug. 30, 1994

[54] MACROCYCLIC LACTONE ANTIBACTERIAL ANTIBIOTIC COMPOUNDS

[75] Inventors: Vinod R. Hegde, Rockaway; Ann C. Horan, Summit, both of N.J.; Joseph A. Marquez, Evergreen, Colo.; Mahesh G. Patel, Verona, N.J.

[73] Assignee: Schering Corporation, Kenilworth, N.J.

[21] Appl. No.: 123,656

[22] Filed: Sep. 20, 1993

[51] Int. Cl.$^5$ .................. A61K 31/34; C07D 307/93
[52] U.S. Cl. ........................... 514/461; 549/297
[58] Field of Search .................. 549/297; 514/461

*Primary Examiner*—C. Warren Ivy
*Assistant Examiner*—A. A. Owens
*Attorney, Agent, or Firm*—Thomas D. Hoffman

[57] ABSTRACT

Novel macrocyclic lactone antibacterials isolated from a culture containing the microorganism *S. aerocolongenes* sub sp. *antibiotica* SCC 1886, ATTC 55003 and their use for treating and/or preventing antibacterial infections, especially Chlamydia infections are disclosed.

19 Claims, No Drawings

MACROCYCLIC LACTONE ANTIBACTERIAL ANTIBIOTIC COMPOUNDS

BACKGROUND OF THE INVENTION

This invention relates to a culture that is the microorganism *Saccharothrix aerocolongenes* subsp. *antibiotica* SCC 1886, ATCC 55003 which produces six novel macrocyclic lactone antibacterial antibiotics. This invention also relates to a method of treating and/or preventing bacterial infections especially Chlamydia-caused infections by use of the macrocyclic lactone antibacterial antibiotic(s) or pharmaceutical compositions containing such macrocyclic lactone antibacterial antibiotics.

Macrocyclic lactone antibiotics are a class of antibacterials including, for example, kijanimicin which is disclosed in U.S. Pat. No. 4,375,542; tetrocarcins which are disclosed, for example, by N. Hirayama et al. in *Tetrahedron Letters*; Vol. 21, (1980) 2259 and Tamaoki et al. in *J. Antibiotics* Vol. 33, (1980) 946; and Antlermycins which are disclosed by K. Kobinata et al. in *J. Antibiotics* (1980) Vol. 33, 244 and 772. No prior art reference of which we are aware discloses the macrocyclic lactone antibacterial antibiotics of this invention.

SUMMARY OF THE INVENTION

The present invention provides a compound represented by formula I

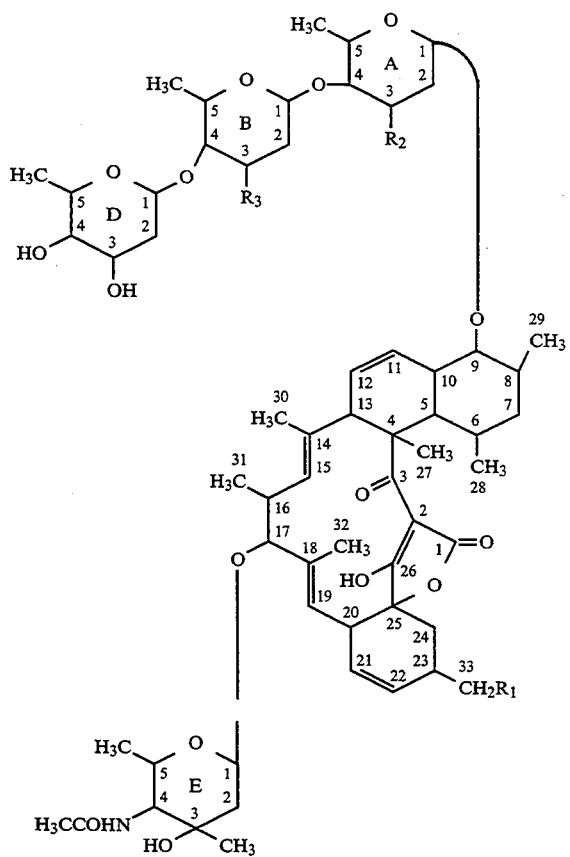

wherein
$R_1=CH_2CH_3$, $R_2=H$, and $R_3=$

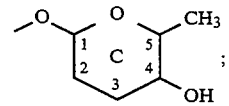

$R_1=CH_3$, $R_2=OH$, and $R_3=$

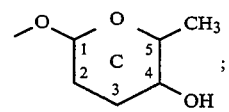

$R_1=CH_2CH_3$, $R_2=OH$, and $R_3=$

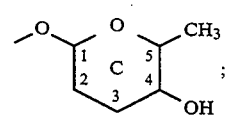

$R_1=CH_3$, $R_2=H$, and $R_3=OH$;
$R_1=CH_3$, $R_2=H$, and $R_3=$

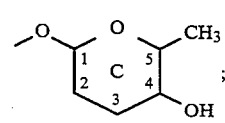

or
$R_1=CH_2CH_3$, $R_2=H$, and $R_3=OH$.

The present invention also provides a method of treating and/or preventing bacterial infections in a mammal which comprises administering an antibacterial effective amount of compound represented by formula I:

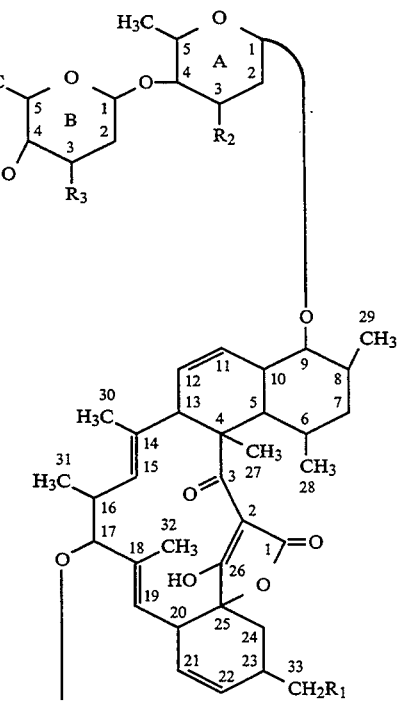

-continued

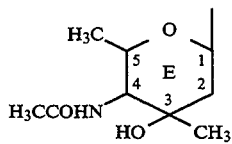

wherein
$R_1 = CH_2CH_3$, $R_2 = H$, and $R_3 =$

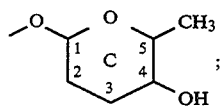

$R_1 = CH_3$, $R_2 = OH$, and $R_3 =$

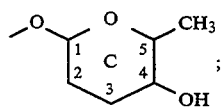

$R_1 = CH_2CH_3$, $R_2 = OH$, and $R_3 =$

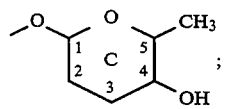

$R_1 = CH_3$, $R_2 = H$, and $R_3 = OH$;
$R_1 = CH_3$, $R_2 = H$, and $R_3 =$

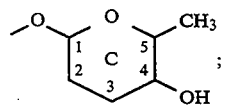

$R_1 = CH_2CH_3$, $R_2 = H$, and $R_3 = OH$; or
or mixtures of compounds of formula I or pharmaceutical compositions thereof.

The present invention further provides a pharmaceutical composition for treating and/or preventing a bacterial infection in mammals which comprises an antibacterial effective amount of a compound of formula 1 or mixtures thereof and a pharmaceutically acceptable carrier therefor.

Finally the present invention provides a biologically pure culture of the microorganism *Saccharothrix aerocolongenis* subsp *antibiotica* SCCC 1886, ATCC 55003, said culture being capable of producing the compounds of formula I in recoverable quantity upon fermentation in an aqueous nutrient medium containing assimilable sources of carbon, nitrogen and inorganic substances.

THE MICROORGANISM

*Saccharothrix aerocolonigenes* subsp. *antibiotica* SCC 1886 was isolated from a soil sample found in Ohio. A viable culture of this microorganism SCC 1886 was deposited on Jan. 4, 1990 in the collection of the American Type Culture Collection (ATCC) in Rockville, Md., where it has been assigned accession number ATCC 55003. Should the deposited culture become lost, destroyed or non-viable during the longer of the thirty (30) year period from the date the culture was deposited or the five (5) year period after the last request for the deposited culture or the effective life of the patent which issues from this application, the culture will be replaced upon notice by applicants or assignee(s) of this application. Subcultures of *Saccharothrix aerocolonigenes* subsp. *antibiotica* SCC 1886, ATCC 55003 are available during the pendency of this application to one determined by the Commissioner of Patents and Trademarks to be entitled thereto under 37 CFR 1.14 and 35 USC 122 and will be available to the public without restriction once a patent based on this application is granted. Use of the microorganism is dependent on the US Patent Laws.

Taxonomic Description of the Producing Strain
*Saccharothrix aerocolonigenes* subsp. *antibiotica* SCC 1886, ATCC 55003

Strain Maintenance

Source materials used for the following taxonomic studies were frozen (−80° C.) preparations of pure cultures of the strain SCC 1886. Inoculum for the biochemical and physiological tests was prepared by adding 1.0 ml of thawed culture suspension to 10 ml of the broth in a test tube which was placed on a rotary shaker (250–300 RPM, 28°–30° C.) for 3 to 5 days. The culture was harvested by centrifugation and, where appropriate, washed three times with distilled water by centrifugation. The final cell pellet so-obtained was resuspended in distilled water to approximately 4 times the packed cell volume. Approximately 0.1 ml of the cell suspension so-formed was used to inoculate all biochemical tests except the lysozyme studies, where the inoculum was a drop of a very dilute cell suspension. Readings of the results were made at weekly intervals over a 2 to 6 week period.

Morphological observations of the culture were made on plates of water agar, inorganic salts-starch agar (ISP 4) and Czapek sucrose agar. Plates were incubated at 28°–30° C. for 2 to 4 weeks. Morphology Strain SCC 1886 is a gram positive, filamentous organism that forms a well-developed moderately branching substitute mycelium with hyphae approximately 0.4 to 0.8 μm in diameter. The substrate mycelium has a tendency to fragment into coccobacillary elements as the culture ages.

Strain SCC 1886 usually produces little visible aerial mycelium. Such aerial mycelium, when present, is usually in the form of scattered white patches. Under 400× magnification, sparse, scattered patches of aerial mycelia are frequently observed. Much of this mycelia is sterile but, an occasional hyphae that has completely fragmented into spores will be observed. Such spore chains are straight to flexuous and vary in length from less than ten spores to frequently more than 50 spores per chain. Such spores are cylindrical and somewhat irregular in size (approximately 0.6–0.8 μm wide×0-.8–4.3 μm long). When aerial mycelia become sufficiently dense on inorganic salts-starch agar, characteristic clumps of interwoven aerial hyphae or "aerial colonies" are sometimes observed. No motile elements were observed in either the substrate or aerial mycelia.

Chemotaxonomy

Purified cell wall preparations of the producing strain SCC 1886 contain meso-diaminopimelic acid, glutamic acid, alanine, galactosamine, glucosamine, muramic acid, galactose, ribose and rhamnose (Cell wall Type III). Whole-cell hydrolysates contain galactose, glucose, mannose, ribose and rhamnose. Phospholipids present were phosphatidylinositol mannosides, phosphatidylinnositol, diphosphatidyiglycerol and phosphatidylethanolamine acylated with hydroxy fatty acids and normal fatty acids (Type PII). No mycolates are present.

Physiological and Biochemical Characteristics

The physiological and biochemical characteristics of the strain SCC 1886 are presented in Table 1. Acid production from carbohydrates and carbohydrate utilization of the Strain SCC 1886 are shown in Table 2.

Macroscopic Description

The growth characteristic of the strain SCC 1886 on various media are presented in Table 3. All plates were incubated at 28° C. and observed at intervals of up to 4 weeks. The common names for the colors were chosen after comparison with color chips from the Methuen Handbook of Colour (Third Edition, Eyre Methuen Ltd., London). The substrate mycelium of strain SCC 1886 varies from pale yellow to brownish orange to light brown. Strain SCC 1886 tends to produce little, if any, visible aerial mycelium. If present, it is as scattered white patches. Under 400× magnification scattered patches of aerial mycelium are sometimes observed on inorganic salts-starch agar, Czapek sucrose agar or glycerol-asparagine agar. The soluble pigments produced by strain SCC 1886 vary from pale yellow to pinkish white to brownish orange.

Conclusion

On the basis of the following characteristics of strain SCC 1886 described above: (1) chemotaxonomic, i.e., that the cell wall contains meso-diaminopimelic acid but no glycine; whole-cell hydrolysates contain galactose and rhamnose; phosphatidylethanolamine is present; and, that mycolic acids are absent, (2) physiological, i.e., that the strains SCC 1880 is aerobic, catalase positive and lysozyme resistant, and (3) morphological, i.e., both aerial and vegative hyphae fragment into ovoid to bacillary nonmotile elements, strain SCC 1886 was placed in the genus Saccharothrix.

The description of strain SCC 1886 was compared with the descriptions of those Saccharothrix species listed on the Approved Lists of Bacterial Names or found in the patent literature: *Saccharothrix australiensis*, *S. aerocolonigenes*, *S. cryophilus*, *S. espanaensis*, *S. mutabilis*, *S. texasensis* and *S waywayandensis*. On the basis of physiological characteristics, strain SCC 1886 was easily differentiated from all the described species except *S. waywandensis* and *S. aerocolonigenes*. Strain SCC 1886 was, therefore, compared directly with *S. aerocolonigenes* ATCC 23870 and *S. waywandensis* NRRL B-16159.

Strain SCC 1886 can be differentiated from *S. wayayandensis* on the basis of morphology. *S. waywayandensis* does not produce the characteristic clumps of interwoven aerial hyphae or "aerial colonies" found in SCC 1886. *S. waywayandensis* also fails to reduce nitrate to nitrite and does not grow at 37° C. or 40° C.

Strain SCC 1886 shares the morphological and many of the physiological characteristics of *S. aerocolonigenes* ATCC 23870 (the type culture for the species). The results of tests for acid production from carbohydrates, carbohydrate utilization and organic acid utilization are similar for the two cultures. Strain SCC 1886 differs from ATCC 23870 in that strain SCC 1886 (1) fails to survive incubation at 50° C. for 8 hours, (2) hydrolyzes arbutin, (3) inhibits the growth of *Micrococcus luteus* 9341 and (4) produces novel antibiotics with activity against Chlamydia.

Strain SCC 1886 differs from ATCC 53586 (SCC 1951) *S. aerocolonigenes* subsp. *copiosa* in that SCC 1886 (1) fails to produce acid from erythritol or sorbitol (2) fails to destroy the chromophore of phenol red and (3) fails to survive incubation at 50° C. for 8 hours.

We, therefore, consider SCC 1886 to be a new subspecies of *Saccharothrix aerocolonigenes* for which we propose the name *S. aerocolonigenes* subsp. *antibiotica* in reference to the novel antibiotics which are produced by the producing strain SCC 1886 of this invention.

TABLE 1

Physiological and Biochemical Characteristics of *Saccharothrix aerocolonigenes* subsp. *antibiotica* SCC 1886, ATCC 55003

| Test | Results |
|---|---|
| Hydrolysis or Decomposition of: | |
| Adenine | − |
| Allantoin | + |
| Arbutin | + |
| Casein | + |
| Elastin | + |
| Esculin | + |
| Gelatin | + |
| Hippurate | + |
| Hypoxanthine | + |
| L-Tyrosine | + |
| Potato starch | + |
| Urea | + |
| Xanthine | − |
| Xylan | + |
| Resistance to Lysozyme | + |
| Production of: | |
| Catalase | + |
| Phosphatase | + |
| Nitrate Reductase | + |
| Formation of Melanin | − |
| Growth at: | |
| 10° C. | + |
| 28° C. | + |
| 35° C. | + |
| 37° C. | + |
| 40° C. | + |
| 42° C. | wv |
| 45° C. | − |
| Growth in the presence of: | |
| 4% NaCl | + |
| 5% NaCl | + |
| 6% NaCl | v |
| 7% NaCl | − |
| Utilization of: | |
| Acetate | + |
| Benzoate | − |
| Citrate | + |
| Formate | + |
| Lactate | + |
| Malonate | + |
| Oxalate | + |
| Propionate | + |
| Succinate | + |
| Tartrate | − |

+ = positive; − = negative; v = variable; wv = weak and variable.

TABLE 2

Carbohydrate Utilization and Acid Production for *S. aerocolonigenes* subsp. *antibiotica* SCC 1886, ATCC 55003

| Carbohydrate | Acid Production | Carbohydrate Utilization[1] |
|---|---|---|
| Adonitol | + | wv |
| L-Arabinose | + | + |
| D-Cellobiose | + | + |
| Dextrin | + | + |
| Dulcitol | − | wv |
| i-Erythritol | − | − |
| D-Fructose | + | + |
| D-Galactose | + | + |
| Glucose | + | + |

TABLE 2-continued

Carbohydrate Utilization and Acid Production for
S. aerocolonigenes subsp. antibiotica SCC 1886, ATCC 55003

| Carbohydrate | Acid Production | Carbohydrate Utilization[1] |
|---|---|---|
| Glycerol | + | + |
| i-Inositol | + | + |
| Inulin | − | − |
| Lactose | + | + |
| Maltose | + | + |
| D-Mannitol | + | + |
| D-Mannose | + | + |
| D-Melezitose | − | − |
| D-Melibiose | + | + |
| α-Methyl-D-glucoside | − | − |
| D-Raffinose | + | wv |
| L-Rhamnose | + | + |
| D-Ribose | + | + |
| Salicin | wv | + |
| D-Sorbitol | − | wv |
| Sucrose | + | + |
| Trehalose | + | + |
| Xylose | + | + |

+ = positive; − = negative; wv = weak and variable.
[1]Basal medium is ISP9

TABLE 3

Description of S. aerolonigenes subsp. antibiotica
ATCC 55003 SCC 1886 on Various Description Media

| Medium | | Growth Characteristics |
|---|---|---|
| Bennett Agar | G: | Fair, translucent, off-white to grayish yellow |
| | AM: | None |
| | SP: | None |
| Glycerol-Asparagine Agar (ISP5) | G: | Poor, translucent, off-white |
| | AM: | None |
| | SP: | None |
| Glucose-Yeast Extract Agar | G: | Good to excellent, grayish yellow (Methuen 4B4) to amber (methuen 4B6) |
| | AM: | None |
| | SP: | Pale yellow-brown |
| Yeast Extract-Malt Extract Agar (ISP2) | G: | Good to excellent, grayish yellow (Methuen 4B4) to brownish orange (Methuen 5C6) |
| | AM: | None |
| | SP: | None |
| Oatmeal Agar (ISP3) | G: | Good, yellowish white (Methuen 3A2) to grayish yellow (Methuen 4B4) |
| | AM: | None |
| | SP: | Pale yellow to yellow-brown |
| Inorganic Salts-Starch Agar (ISP4) | G: | Good, yellowish white (Methuen 4A2) to grayish yellow (Methuen 4B4) |
| | AM: | None |
| | SP: | Pale yellow-brown (variably present) |
| Starch Agar (Waksman #21) | G: | Good, pale yellow (Methuen 4A3) to grayish orange (Methuen 5B4) |
| | AM: | None |
| | SP: | Pinkish white (Methuen 7A2) to grayish orange (Methuen 6B4) |
| Water Agar | G: | Poor, translucent, off-white |
| | AM: | None |
| | SP: | None |
| Peptone-Yeast Extract Iron Agar (ISP6) | G: | Fair, grayish yellow (Methuen 4B4) |
| | AM: | None |
| | SP: | Pale yellow-brown |
| Czapek-Sucrose Agar | G: | Good to excellent, yellow-brown turning light brown (Methuen 6D6) to brownish orange (Methuen 5C5) |
| | AM: | Sparse, white |
| | SP: | Brownish orange (Methuen 6C6 to 6C8) |
| ATCC Medium 172 | G: | Excellent, brownish orange (Methuen 5C5 to 5C6) |
| | AM: | None |
| | SP: | Yellow-brown to brownish orange (Methuen 6C7) |

G = Vegative growth; AM = Aerial mycelium; SP = Soluble pigment

The Fermentation

S. aerocolonigenes subsp. antibiotica SCC 1886 when fermented under controlled conditions in an aqueous medium containing assimilable source of carbon, nitrogen and inorganic substances produces recoverable quantities of the antibacterial compounds of formula I.

The fermentation which produces the antibacterials is initiated by the production of an inoculum which is usually produced in two or more stages. A suitable medium for preparing such inoculum is set forth below as Medium A and the pH is maintained at about 6.4 to 8.2, preferably about 7.0. The proper pH ranges are usually maintained by incorporation of suitable buffers, such as calcium carbonate into the medium. The inoculum is grown at a temperature of about 27° to 35°, preferably about 30° C.

The media were sterilized and cooled prior to inoculation and fermentation stock cultures were stored as frozen whole broths at subzero temperatures prior to use.

Inoculation Preparation (First Stage)

Inoculum preparation was carried out in two stages for large scale fermentation (10 L). Suitable nutrients for preparing the inocula are listed below:

| Inoculum Medium A | |
|---|---|
| Ingredient | g/L |
| Glucose | 10.0 |
| Trehalose | 10.0 |
| Enzymatically hydrolyzed casein | 5.0 |
| Soy flour | 5.0 |
| Yeast extract | 5.0 |
| Calcium carbonate | 2.0 |
| Tap water | 1L |

Two and a half milliliters of freshly-thawed whole broth were used to inoculate 70 mL of the above-listed inoculum Medium A. The 250 mL Erlenmeyer flasks were incubated at 30° C. for 48 hours on a shaker at 300 rpm and having a 2 inch throw.

Second Inoculum Preparation

A 2 L Erlenmeyer flask containing 500 mL of sterile inoculum Medium A was inoculated using 10% of the first stage inoculum. The procedure for the first inoculum stage was followed.

Antibacterial Production (fermentation) Stage

The following fermentation Medium B has been found to produce the compounds of this invention:

| Fermentation Medium B | |
|---|---|
| Ingredient | g/L |
| PD 650 Dextrin | 30.0 |
| Molasses | 10.0 |
| Soluble starch | 5.0 |

| Fermentation Medium B | |
| --- | --- |
| Ingredient | g/L |
| Tap water | 1L |
| Pre-sterilization | pH 6.5 |

500 mL of the second stage inoculum were used to inoculate 10 L of the fermentation Medium B. The fermentation was carried out for 120 hours at 30° C. in a 10 L NBS Microgen fermenter with agitation and aeration at 350 rpm and 3.5 Lpm, respectively.

No pH adjustment was made to the mixture, but monitoring shows a pH range from about 6.4 to about 8.1 over the course of the 120 hours of mixing.

Production of the antibacterial antibiotics was monitored over time by agar diffusion assay using *Micrococcus luteus* as the test organism.

Isolation and Purification

The six antibacterial antibiotics compounds of formula I were isolated by extracting the whole fermentation broth with two volumes of an immiscible organic solvent, e.g. ethyl acetate. The extracts were combined, dried and the solvent is evaporated to form a residue. The residue was dissolved in a minimum volume of acetone and a complex of antibacterials was precipitated from hexane in the form of a solid.

The solid antibacterial complex so-formed was subjected to preparative High Performance Liquid Chromatography (HPLC) on a silica gel cartridge using chloroform:methanol (95:5 v/v) as the eluting solvent to produce an enriched antibacterial complex containing six components. The antibacterial complex was further purified by preparative reverse-phrase HPLC on a YMC C-18 column (5×30 cm) using an elution solvent of methanol:0.01N $NaH_2PO_4$ (7:3 v/v). The six antibacterial compounds represented by formula I were isolated from the active fractions in substantially chemically pure form (>99% pure) by removing the methanol and extracting the solids so-formed with ethyl acetate. The organic layers were washed with brine, dried and the organic solvent was evaporated to obtain the six individual antibacterials represented by formula I.

Structural Determination

The structure formulas of the six antibacterial compounds were determined by interpretation of the physiochemical data which are tabulated separately herein below. The UV spectra of each of the six are similar and indicative that the six antibacterials each possess a similar chromophore and macrocyclic lactone aglycone structure. The molecular formulas of each compound was determined by high resolution mass spectrometric measurements. The $^{13}C$ NMR confirmed the number of carbons in each molecular formula which was determined by mass spectrometric measurements. The structural formulas listed hereinbelow for each of the six antibacterials were determined by analysis of the proton NMR, $^{13}C$ NMR, COSY spectral data and mass spectral fragments.

PHYSICO-CHEMICAL PROPERTIES

Ia

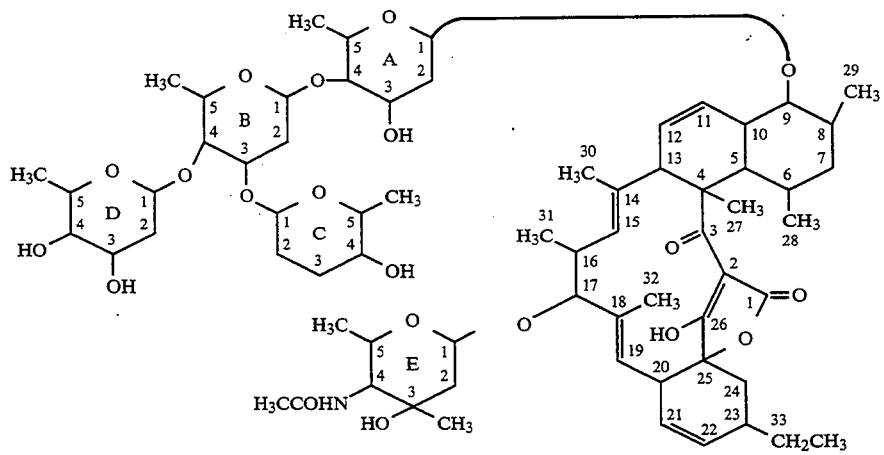

UV(MeOH) λ max, nm: 205(13700), 240(13050), 267(12115)

+HCl: 207(38900), 262(10375)

+NaOH: 211(53030), 266(12800), 366(990)

IR (KBr) ν max, $cm^{-1}$: 3440, 2975, 2930, 1755, 1630, 1555, 1420, 1385, 1060, 975

FAB MS: 1240(M+H)+, 1126, 978, 866, 736, 533.

High Res. MS: Found: 1262. 6877(M+Na)+ Calcd. for $C_{67}H_{101}NO_{20}Na$ 11262.6815

$^1H$ NMR(CDCl₃) δ:5.92(dt, J=10, 0.5 Hz, 1H), 5.83(d, J=10 Hz, 1H), 5.74(d, J=1 Hz, 1H), 5.3(d, J=10 Hz, 1H), 5.27(m, 1H), 5.25(d, J=10 Hz, 1H), 5.18(d, J=11 Hz, 1H), 5.15(d, J=5 Hz, 1H), 4.96(dd, J=10, 2 Hz,1H), 4.94(s, 1H), 4.82(d, J=5 Hz, 1H), 4.57(dd, J=10, 2 Hz, 1H), 4.26(m, 2H), 4.12(q, J=7 Hz, 1H), 4.02(m,3H), 3.9(m, 2H), 3.74(d, J=10 Hz, 1H) 3.75-3.6(m,3H), 3.55(d, J=11 Hz, 1H), 3.47(dd, 11, 5 Hz, 1H), 3.4(dd, J=10, 3 Hz, 1H), 3.35(d, J=4 Hz, 1H), 3.32(dd, J=10, 4 Hz, 1H), 3.2-3.4(d, 2H), 2.45(t, J=8 Hz, 1H), 2.37(dd, J=16, 2 Hz, 1H), 2.2-2.35(m, 4H), 2.16(dd, J=16, 2 Hz, 1H), 2.08(s, 3H), 2.05(m, 1H), 1.7-2.0(several protons), 1.84(s, 3H), 1.64(s, 3H), 1,64-1.44(m, 5H), 1.44(s, 3H), 1.36(s, 3H), 1.32(d, J=6 Hz, 3H), 1.28(d, J=6 Hz, 3H), 1.26(d, J=6 Hz, 3H), 1.24(s, 3H), 1.20(d, J=6 Hz, 3H), 1.12(d, J=7 Hz, 3H), 1.07(d, J=7 Hz, 3H), 1.0(d, J=7 Hz, 3H), 0.96(t, J=7 Hz, 3H), 0.64(d, J=5 Hz, 3H)

Ib

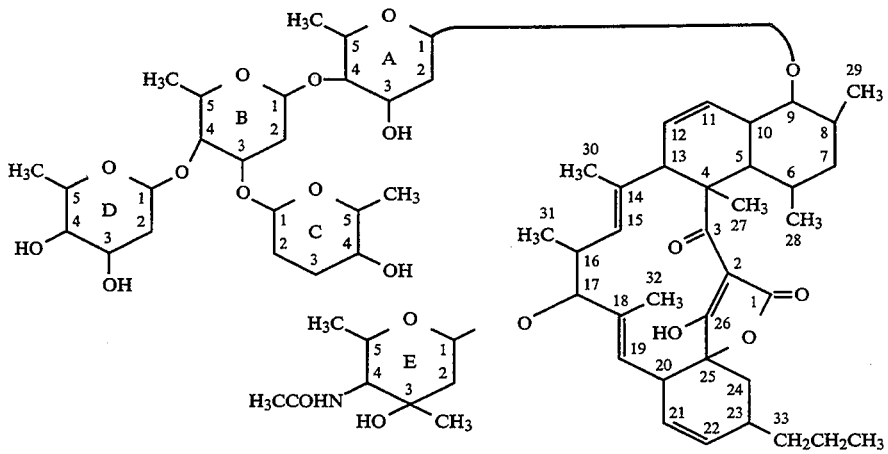

UV(MeOH) λ max, nm: 205, 240, 267

IR(KBr) v max, cm⁻¹: 3430, 2975, 2925, 1765, 1730, 1555, 1455, 1385, 1125, 1060, 990

FAB MS: 1254(M+H)+, 1140, 1011, 993, 880, 750, 547

High Res. MS: Found (M+H)+: 1276.7004 calcd. for $C_{68}H_{103}NO_{20}Na$: 1276.6971

¹H NMR(CDCl₃) δ: 5.78(d, J=11 Hz, 0.5 Hz, 1H), 5.66(d, J=10 Hz, 1H), 5.62(d, J=11 Hz, 1H), 5.3(d, J=10 Hz, 1H), 5.3(m, 1H), 5.15(d, J=9 Hz, 1H), 5.07(d, J=11 Hz, 1H), 5.03(d, J=4 Hz, 1H), 4.97(m, 1H), 4.8(m, 1H), 4.7(d, J=5 Hz, 1H), 4.45(dd, J=10, 2 Hz, 1H), 4.15(b, 1H), 4.0(dq, J=7, 0.5 Hz, 1H), 3.9(m, 4H), 3.8(s, 1H), 3.58(d, J=10 Hz, 1H), 3.4(df, J=11, 0.5 Hz, 1H), 3.37(m, 1H), 3.3(m, 1H), 3.15(m, 4H), 2.4(dt, J=9, 2 Hz, 1H), 2.3-2.05(several protons), 1.97(s, 3H), 1.7(d, J=14 Hz, 2H), 2.05-1.4(several protons), 1.5(s, 3H), 1.3(s, 3H), 1.25(s, 3H), 1.25(d, J=7 Hz, 3H), 1.2(s, 3H), 1.0(s, J=7 Hz, 3H), 1.0(m, 2H), 0.9(d, J=7 Hz, 3H), 0.82(t, J=7 Hz, 3H), 1.04-1.08(several protons), 0.65(d, J=5 Hz, 3H)

UV(MeOH) λ max, nm: 205, 240, 267

IR (KBr) v max, cm⁻¹: 3435, 2980, 2930, 1765, 1665, 1635, 1455, 1385, 1125, 1070, 985

FAB MS: 1110(M+H)+, 980, 850, 736, 533

High Res. MS: Found (M+H)+ 1110.6356 Calcd. for $C_{61}H_{92}NO_{17}$ 1110.6365

¹H NMR(CDCl₃) δ: 5.9(dt, J=10, 3 Hz, 1H), 5.86(d, J=11 Hz, 1H), 5.74(d, J=11 Hz, 1H), 5.37(m, 1H), 5.2(d, J=9 Hz, 1H), 5.14(dd, J=11, 0.5 Hz, 1H), 5.03(d, J=4 Hz, 1H), 4.92(dd, J=10, 2 Hz, 1H), 4.99(s, 1H), 4.55(dd, J=8, 2 Hz, 1H), 4.07(dd, J=6, 4 Hz, 1H), 3.89(s, 1H), 3.83(dd, J=9, 10 Hz, 1H), 3.74(dd, J=6, 1.5 Hz, 1H), 3.65(d, J=10 Hz, 1H), 3.25(dd, J=10, 3 Hz, 1H), 2.56(b, 1H), 2.46(dt, J=2, 9 Hz, 1H), 2.34(b, 1H), 2.3(t, J=7 Hz, 1H), 2.22(b, 2H), 2.06-2.18(m, 2H), 2.2(s, 3H), 2.02-1.92(m, 4H), 1.86-1.62(several protons), 1.6(s, 3H), 1.62-1.42(m, 2H), 1.4(s, 3H), 1.34(s, 3H), 1.28(d, J=6 Hz, 3H), 1.26(d, J=6 Hz, 3H), 1.24(s, 3H), 1.23 (d, J=6 Hz, 3H), 1.09(d, J=7.5 Hz, 3H), 1.06(d, J=7 Hz, 3H), 0.97(d, J=7 Hz, 3H), 0.96(t, J=7 Hz, 3H), 0.64(d, J=5 Hz, 3H)

Ic

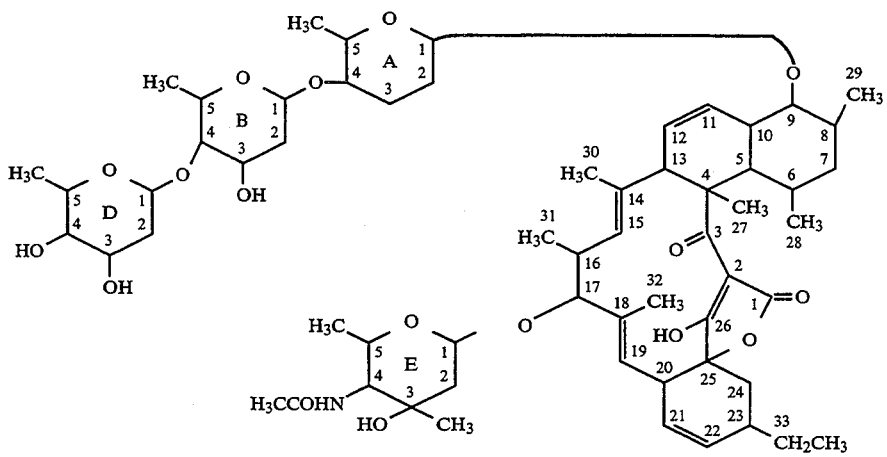

Id

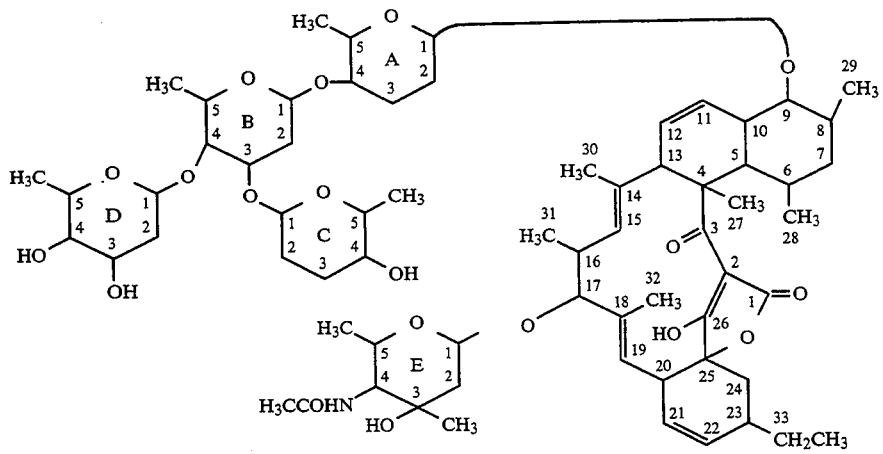

UV(MeOH) λ max, nm: 205, 240, 267

IR (KBr) v max, cm$^{-1}$: 3440, 2975, 2930, 1755, 1665, 1630, 1455, 1375, 1125, 1055, 975

FAB MS: 1224, 1111, 959, 850, 736, 533

High Res. MS: Found (M+Na)$^+$ 1246.6859 Calcd. for $C_{67}H_{101}NO_{19}$ 1246.6865

$^1$H NMR(CDCl$_3$) δ: 5.9(dt, 10, 2 Hz, 1H), 5.8(d, J=10 Hz, 1H), 5.75(d, J=10 Hz, 1H), 5.38(m, 2H), 5.22(d, J=9 Hz, 1H), 5.16(d, J=11 Hz, 1H), 5.08(d, J=11 Hz, 1H), 5.03 (d, J=4 Hz, 1H), 4.95(dd, J=10, 2 Hz, 1H), 4.92(d, J=4 Hz, 1H), 4.8(d, J=1 Hz, 1H), 4.55(dd, J=10, 2 Hz, 1H), 4.27(dd, J=6, 1 Hz, 1H), 4.1(m,2H), 3.89(s, 1H), 3.85(m, 2H), 3.67(d, J=10 Hz, 1H), 3.63(m, 2H), 3.53(dd, J=11, 5 Hz, 2H), 3.45(dd, J=10, 3 Hz, 1H), 3.37(d, J=5 Hz, 2H) 3.31(m, 1H), 3.23(dd, J=10, 3 Hz, 2H), 2.47(dt, J=7, 2 Hz, 1H), 2.34-2.1(m, 6H), 2.05(s, 3H), 2.1-2.2(m, 2H), 2.0(m, 3H), 1.93-1.64(several protons), 1.6(s, 3H), 1.64-1.4(m, 5H), 1.41(s, 3H), 1.36(s, 3H), 1.31(d, J=6 Hz, 3H), 1.07(d, J=5 Hz, 3H), 0.99(d, J=6 Hz, 3H), 0.97(t, J=7 Hz, 3H), 0.65(d, J=4 Hz, 3H)

UV(MeOH) λ max, nm: 205, 240, 267

IR (KBr) v max, cm$^{-1}$: 3430, 2965, 2930, 1750, 1630, 1455, 1440, 1385, 1125, 1070, 985

FAB MS: 1124,(M+H)$^+$, 995, 864, 750, 547

MOL FORMULA: $C_{62}H_{93}NO_{17}$ $^1$H NMR (CDCl$_3$) δ: 5.87(dt, J=10 Hz, 1H), 5.77(d, J=10 Hz, 1H), 5.74(d, J=10 Hz, 1H), 5.37(m, 2H), 5.22(d, J=9 Hz, 1H), 5.16(d, J=11 Hz, 1H), 5.03(d, J=4 Hz, 1H), 4.93(dd, J=10, 2 Hz, 1H), 4.8(d, J=0.5 Hz, 1H), 4.55(dd, J=10, 2 Hz, 1H), 4.2(m, 1H), 4.1(m, 3H), 3.89(s, 1H), 3.84(dt, J=9, 3 Hz, 1H), 3.75(dt, J=10, 3 Hz, 1H), 3.65(m, 3H), 3.54(m, 2H), 3.36(m, 3H), 3.26(s, 1H), 3.25(dd, J=7, 3 Hz, 1H), 2.47(dt, J=9, 2 Hz, 1H) 2.4-2.25(m, 3H), 2.25-2.1(m, 4H), 2.05(s, 3H), 2.1-1.75(m, several protons), 1.6(s, 3H), 1.75-1.46(several protons), 1.41 (s, 3H), 1.35(s, 3H), 1.46-1.38(m, 2H), 1.38-1.33(m, 1H), 1.29(d, J=7 Hz, 3H), 1.27(d, J=7 Hz, 3H), 1.25(s, 3H), 1.24(d, J=7 Hz, 3H), 1.14(m, 2H), 1.1 (d, J=9 Hz, 1H), 1.07(d, J=7 Hz, 3H), 0.98(d, J=7 Hz, 3H), 0.92(t, J=7 Hz, 3H), 0.65(d, J=4 Hz, 3H)

Ie

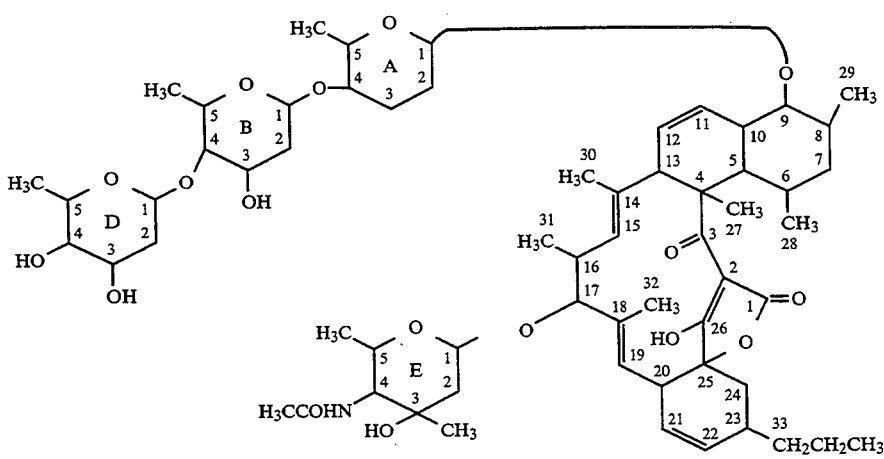

If

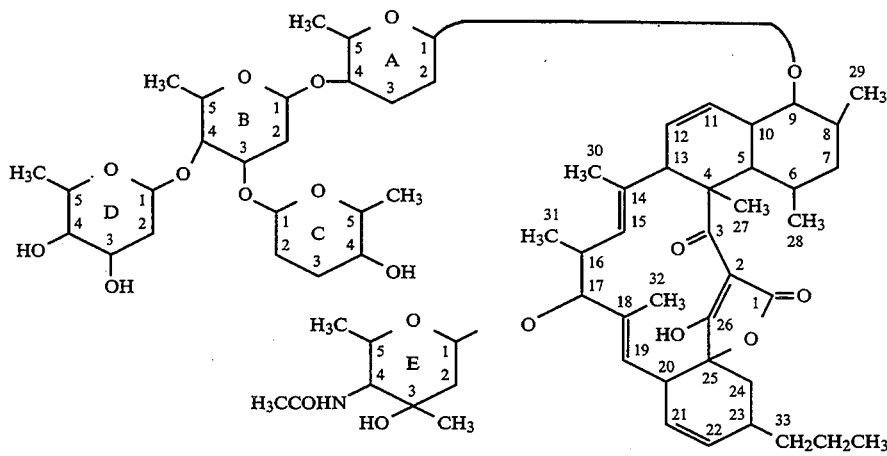

UV(MeOH) λ max, nm: 205, 240, 267

IR(KBr) ν max, cm$^{-1}$: 3435, 2965, 2930, 1715, 1630, 1455, 1410, 1385, 1125, 1055, 990 cm$^{-1}$

FAB MS: 1238(M+H)$^+$, 1124, 864, 750, 679, 619, 547

MOL FORMULA: $C_{68}H_{103}NO_{19}$ $^1$H NMR(CDCl$_3$) δ: 5.87(dt, J=11, 2 Hz, 1H), 5.83(d, J=10 Hz, 1H), 5.75(d, J=10 Hz, 1H), 5.37(m, 2H), 5.22(d, J=9 Hz, 1H), 5.16(d, J=10.5 Hz, 1H), 5.03(d, J=4 Hz, 1H), 4.95(dd, J=10, 2 Hz, 1H), 4.92(s, 1H), 4.79(s, 1H), 4.55(dd, J=10, 2 Hz, 1H), 4.26(dd, J=10, 2 Hz, 1H), 4.2(dt, J=3, 3 Hz, 1H), 4.08(dt, J=7, 9 Hz, 1H), 3.9(s, 1H), 3.85(m, 2H), 3.65(m, 5H), 3.54(dd, J=11, 5 Hz, 1H), 3.45(dd, J=10, 3 Hz, 1H), 3.38(m, 1H), 3.26(dd, J=7, 3 Hz, 1H), 3.24(s, 1H), 2.45(dt, J=10, 2 Hz, 1H), 2.4-2.25(m, 2H), 2.2(m, 3H), 2.05(s, 3H), 1.95(m, 2H), 1.9-1.5 (several protons,), 1.5(s, 3H), 1.41(s, 3H), 1.5-1.37(m, 2H), 1.35(s, 3H), 1.3(d, J=7 Hz, 3H), 1.27(d, J=7 Hz, 3H), 1.25(s, 3H), 1.23(d, J=5 Hz, 3H), 1.14(d, J=7 Hz, 3H), 1.1 (d, J=7 Hz, 3H), 1.07(d, J=7 Hz, 3H), 0.98(d, J=7 Hz, 3H), 0.92(t, J=7 Hz, 3H), 0.64(d, J=5 Hz, 3H)

AGLYCONE OF Ia

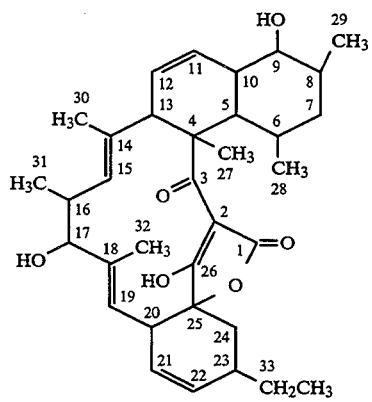

UV(MeOH) λ max, nm: 215, 247, 263

IR(KBr) ν max, cm$^{-1}$: 3459, 2956, 2924, 1751, 1738, 1635, 1448, 1377, 984

FAB MS: 551 (M+H)$^+$

High Res MS: MW Found: 533.3267 calc for $C_{34}H_{46}O_6$: 533.3285

$^1$H NMR(CDCl$_3$) δ: 6.07(dt, J=10, 1 Hz, 1H), 5.95(dt, J=10, 2 Hz, 1H), 5.46(m, 2H), 5.32(dt, J=10, 0.5 Hz, 1H), 5.24(d, J=10 Hz, 1H), 3.9(s, 1H), 3.68(dd, J=10, 5 Hz, 1H), 3.58(ddd, J=11, 4, 2 Hz, 1H), 3.47(d, J=5 Hz, 1H), 2.55(m, 1H), 2.3(m, 3H), 2.05(m, 2H), 1.86(d, J=16 Hz, 1H), 1.7(m, 1H), 1.6(several protons), 1.43(s, 3H), 1.04(d, J=7 Hz, 3H). 1.00(d, J=7 Hz, 3H), 0.98(t, J=7 Hz, 3H), 0.65(d, J=5 Hz, 3H)

AGLYCONE WITH E-SUGAR OF Ia

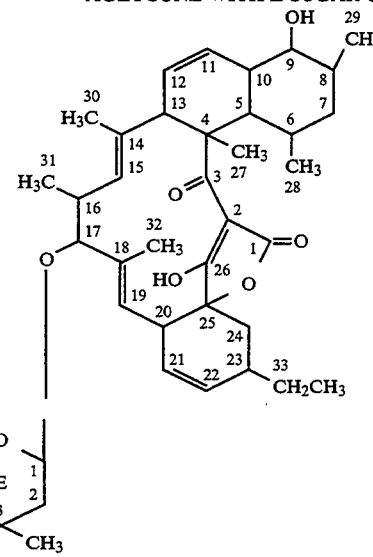

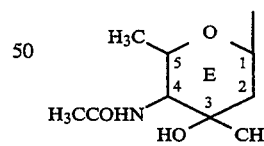

UV(MeOH) λ max, nm: 215, 242, 265

IR(KBr) ν max, cm$^{-1}$: 3433, 2962, 2930, 1764, 1673, 1628, 1454, 1370, 1061

FAB MS: 736(M+H)$^+$

High Res MS: Found: (M+H)$^+$ 736.4408 Calc for $C_{43}H_{62}NO_9$: 736.4424

$^1$H NMR(CDCl$_3$) δ: 6.02(d, J=10 Hz, 1H), 5.92(dt, J=10, 1 Hz, 1H), 5.8(d, J=10 Hz, 1H), 5.4(m, 2H), 5.23(d, J=9 Hz, 1H), 5.17(d, J=10.5 Hz, 1H), 4.55(dd, J=10, 2 Hz, 1H), 4.1 (dt, J=6, 1 Hz, 1H), 3.89(s, 1H), 3.68(d, J=10 Hz, 1H), 3.64(m, 2H), 3.54(dq, J=11, 2 Hz, 1H), 3.39(d, J=5 Hz. 1H). 2.48(m, 1H), 2.28(m, 3H), 2.06(s, 3H), 1.82(t, J=4 Hz, 2H), 1.72(dt, J=8, 7 Hz, 1H), 1.63(s, 3H), 1.58-1.4(several protons), 1.44(m, 1H), 1.4(s, 3H), 1.37(s, 3H), 1.25(s, 3H), 1.06(d, J=6 Hz, 3H), 1.04(d, J=8 Hz, 3H), 0.98(d, J=7 Hz, 3H), 0.96(t, J=7 Hz, 3H), 0.66(d, J=5 Hz, 3H)

AGLYCONE OF Ib

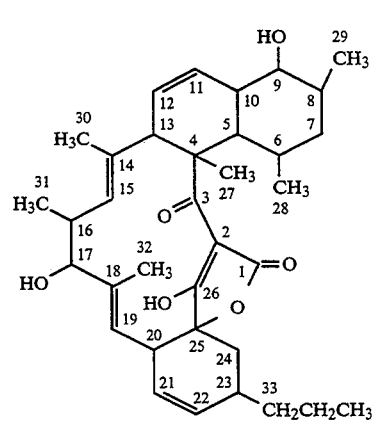

UV(MeOH) λ max, nm: 215, 249, 265
IR(KBr) ν max, cm$^{-1}$: 3459, 2962, 2937, 1764, 1750, 1622, 1583, 1454, 1377, 984
FAB MS: 565(M+H)$^+$, 547
MOL FORMULA : $C_{35}H_{48}O_6$
$^1$H NMR(CDCl$_3$) δ: 6.03(d, J=10 Hz, 1H), 5.9(dt, J=10, 1 Hz, 1H), 5.43(m, 2H), 5.28(d, J=10.5 Hz, 1H), 5.22(d, J=10 Hz, 1H), 3.88(s, 1H), 3.66(dd, J=10, 5 Hz, 1H), 3.55(dq, J=10.5, 2 Hz, 1H), 3.45(d, J=5 Hz, 1H), 2.53(dt, J=4, 1 Hz, 1H), 2.31 (m, 3H), 2.05(m, 2H), 1.82(d, J=15 Hz, 1H), 1.8–1.46(several protons), 1.61 (s, 3H), 1.42(s, 3H), 1.4(m, 1H), 1.39(s, 3H), 1.26(m, 1H), 1.04(d, J=7 Hz, 3H), 1.01(d, J=7H, 3H), 0.92(t, J=7 Hz, 3H). 0.65(d, J=5 Hz, 3H)

AGLYCONE WITH E-SUGAR OF Ib

-continued

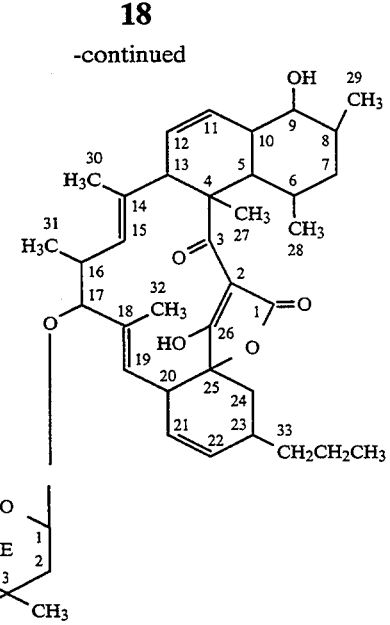

UV(MeOH) λ max, nm: 215, 243, 264
IR(KBr) ν max, cm$^{-1}$: 3433, 2962, 2924, 1755, 1660, 1454, 1383, 1061, 984
FAB MS: 750(M+H)$^+$
MOL FORMULA: $C_{44}H_{63}NO_9$
$^1$H NMR(CDCl$_3$) δ: 6.03(d, J=10 Hz, 1H), 5.89(dt, J=10, 1 HZ, 1H), 5.82(d, J=10 Hz, 1H), 5.4(m, 2H), 5.23(d, J=10.5 Hz, 1H), 5.18(d, J=10.5 Hz, 1H), 4.56(dd, J=10, 2 Hz, 1H), 4.10(dt, J=6, 1 Hz, 1H), 3.9(s, 1H), 3.68(d, J=10 Hz, 1H), 3.65(m, 1H), 3.53(dq, 11, 2 Hz, 1H), 3.38(d, J=5 Hz, 2.48(m, 1H), 2.3 (m, 3H), 2.06(s, 3H), 1.9–1.7(m, 4H), 1.62(s, 3H) 1H), 1.7–1.3(several protons), 1.42(s, 3H), 1.39(s, 3H), 1.25(s, 3H), 1.08(d, J=7 Hz, 3H), 1.03(d, J=7 Hz, 3H), 1.00(d, J=7 Hz, 3H), 0.92(t, J=7 Hz, 3H), 0.65(d, J=5 Hz, 3H)

TABLE 4

$^{13}$C NMR Chemical shifts of different components Ia–If from the culture 85-05857

| Carbon No. | Kijani-mycin | Ia | Ib | Ic | Id | Ie | If |
|---|---|---|---|---|---|---|---|
| C-1 | 167.1(s) | 167.2(s) | 167.2(s) | 167.2(s) | 167.1(s) | 167.1(s) | 167.1(s) |
| C-2 | 109.9(s) | 101.7(s) | 101.7(s) | 101.6(s) | 101.6(s) | 101.7(s) | 101.6(s) |
| C-3 | 206.2(s) | 206.2(s) | 206.2(s) | 206.1(s) | 206.1(s) | 206.2(s) | 206.2(s) |
| C-4 | 51.0(s) | 50.8(s) | 50.8(s) | 50.8(s) | 50.8(s) | 50.8(s) | 50.8(s) |
| C-5 | 31.3(d) | 31.3(d) | 31.3(d) | 31.2(s) | 31.2(s) | 31.2(s) | 31.2(s) |
| C-6 | 27.9(d) | 27.7(d) | 27.7(d) | 27.6(d) | 27.6(d) | 27.7(d) | 27.7(d) |
| C-7 | 41.6(t) | 41.7(d) | 41.8(t) | 41.7(t) | 41.7(t) | 41.7(t) | 41.7(t) |
| C-8 | 38.5(d) | 34.5(d) | 34.5(d) | 34.3(d) | 34.3(d) | 34.4(d) | 34.3(d) |
| C-9 | 84.5(d) | 84.3(d) | 84.3(d) | 83.6(d) | 83.6(d) | 83.6(d) | 83.6(d) |
| C-10 | 34.8(d) | 38.3(d) | 38.5(d) | 38.4(d) | 38.4(d) | 38.4(d) | 38.4(d) |
| C-11 | 125.8(d) | 125.8(d) | 125.8(d) | 125.6(d) | 125.6(d) | 125.6(d) | 125.6(d) |
| C-12 | 126.7(d) | 126.8(d) | 126.8(d) | 126.7(d) | 126.7(d) | 126.8(d) | 126.7(d) |
| C-13 | 53.2(d) | 53.5(d) | 53.5(d) | 53.4(d) | 53.4(d) | 53.4(d) | 53.4(d) |
| C-14 | 135.7(s) | 134.4(s) | 134.4(s) | 134.3(s) | 134.3(s) | 134.3(s) | 134.4(s) |
| C-15 | 123.6(d) | 130.0(d) | 130.1(d) | 129.9(d) | 129.9(d) | 129.9(d) | 129.9(d) |
| C-16 | 31.1(t) | 35.0(d) | 32.9(d) | 34.9(d) | 34.9(d) | 32.8(d) | 32.8(d) |
| C-17 | 78.4(d) | 83.4(d) | 83.4(d) | 83.4(d) | 83.4(d) | 83.3(d) | 83.4(d) |
| C-18 | 137.1(s) | 138.4(s) | 138.4(s) | 138.3(s) | 138.3(s) | 138.3(s) | 138.3(s) |
| C-19 | 121.5(d) | 125.7(d) | 125.7(d) | 125.6(d) | 125.6(d) | 125.5(d) | 125.5(d) |
| C-20 | 43.1(d) | 43.3(d) | 43.3(d) | 43.2(d) | 43.2(d) | 43.3(d) | 43.2(d) |
| C-21 | 119.3(d) | 118.9(d) | 118.9(d) | 118.8(d) | 118.8(d) | 118.9(d) | 118.8(d) |
| C-22 | 141.5(s) | 130.9(d) | 131.1(d) | 130.8(d) | 130.8(d) | 131.0(d) | 131.0(d) |
| C-23 | 40.2(d) | 39.6(d) | 39.6(d) | 39.6(d) | 39.6(d) | 39.6(d) | 39.5(d) |
| C-24 | 35.5(t) | 34.3(t) | 34.3(t) | 35.1(t) | 35.1(t) | 35.1(t) | 35.1(t) |
| C-25 | 83.3(s) | 82.9(s) | 82.9(s) | 82.8(s) | 82.8(s) | 82.8(s) | 82.8(s) |
| C-26 | 201.5(s) | 202.1(s) | 202.2(s) | 202.0(s) | 202.0(s) | 202.1(s) | 202.0(s) |
| C-27 | 20.2(q) | 18.9(q) | 19.0(q) | 18.6(q) | 18.6(q) | 18.6(q) | 18.6(q) |
| C-28 | 22.2(q) | 22.3(q) | 22.3(q) | 22.2(q) | 22.2(q) | 22.2(q) | 22.3(q) |
| C-29 | 14.0(q) | 14.2(q) | 14.3(q) | 14.1(q) | 14.1(q) | 14.1(q) | 14.1(q) |
| C-30 | 15.1(q) | 15.3(q) | 17.1(q) | 15.2(q) | 15.2(q) | 15.2(q) | 15.2(q) |

TABLE 4-continued

13C NMR Chemical shifts of different components Ia–If from the culture 85-05857

| Carbon No. | Kijani-mycin | Ia | Ib | Ic | Id | Ie | If |
|---|---|---|---|---|---|---|---|
| C-31 | 13.7(q) | 15.2(q) | 15.3(q) | 15.1(q) | 15.1(q) | 15.1(q) | 15.1(q) |
| C-32 | 64.4(t) | 13.1(q) | 13.1(q) | 13.1(q) | 13.1(q) | 13.1(q) | 13.1(q) |
| C-33 | 15.1(q) | 28.8(t) | 38.1(t) | 28.7(t) | 28.7(t) | 38.0(t) | 38.0(t) |
| C-34 | — | 12.7(q) | 21.1(t) | 12.6(q) | 12.6(q) | 21.1(t) | 21.1(t) |
| C-35 | — | — | 14.1(q) | — | — | 14.0(q) | 14.0(q) |
| C-1A | 98.2(d) | 98.1(d) | 98.1(d) | 98.5(d) | 98.5(d) | 98.5(d) | 98.5(d) |
| C-2A | 29.9(t) | 29.8(t) | 29.8(t) | 22.8(t) | 22.8(t) | 22.8(t) | 22.8(t) |
| C-3A | 66.8(d) | 66.5(d) | 66.5(d) | 29.1(t) | 29.1(t) | 29.1(t) | 29.1(d) |
| C-4A | 71.8(d) | 71.7(d) | 71.7(d) | 82.4(d) | 82.5(d) | 82.5(d) | 82.5(d) |
| C-5A | 65.1(d) | 65.1(d) | 65.1(d) | 68.3(d) | 68.3(d) | 68.4(d) | 68.3(d) |
| C-6A | 17.9(q) | 17.8(q) | 18.5(q) | 18.1(q) | 18.4(q) | 18.1(q) | 18.4(q) |
| C-1B | 90.8(d) | 91.0(d) | 91.0(d) | 91.9(d) | 91.9(d) | 91.9(d) | 91.9(d) |
| C-2B | 29.7(t) | 36.9(t) | 36.9(t) | 37.8(t) | 36.7(t) | 37.8(t) | 36.7(d) |
| C-3B | 62.6(d) | 70.4(d) | 70.4(d) | 68.2(d) | 68.0(d) | 68.3(d) | 68.0(d) |
| C-4B | 79.6(d) | 75.2(d) | 75.2(d) | 74.5(d) | 75.1(d) | 74.5(d) | 75.1(d) |
| C-5B | 67.1(d) | 68.1(d) | 68.1(d) | 69.4(d) | 70.3(d) | 69.3(d) | 70.3(d) |
| C-6B | 17.9(q) | 18.1(q) | 18.1(q) | 17.7(q) | 17.7(q) | 17.7(q) | 17.7(q) |
| C-1C | 92.2(d) | 92.0(d) | 92.0(d) | — | 91.9(d) | — | 91.9(d) |
| C-2C | 34.4(t) | 27.4(t) | 27.4(t) | — | 27.4(t) | — | 27.4(t) |
| C-3C | 67.5(d) | 30.0(t) | 30.1(t) | — | 29.7(t) | — | 29.7(t) |
| C-4C | 72.4(d) | 71.9(d) | 72.0(d) | — | 71.7(d) | — | 71.7(d) |
| C-5C | 64.9(d) | 63.9(d) | 63.9(d) | — | 63.9(d) | — | 63.9(d) |
| C-6C | 17.9(q) | 17.8(q) | 18.3(q) | — | 17.7(q) | — | 17.7(q) |
| C-1D | 99.8(d) | 98.4(d) | 98.4(d) | 98.9(d) | 98.9(d) | 98.8(d) | 99.0(d) |
| C-2D | 36.8(t) | 40.3(t) | 40.3(t) | 40.2(t) | 40.2(t) | 40.3(t) | 40.2(t) |
| C-3D | 63.8(d) | 65.5(d) | 65.5(d) | 66.2(d) | 66.2(d) | 66.3(d) | 66.2(d) |
| C-4D | 82.6(d) | 82.3(d) | 82.3(d) | 72.7(d) | 74.5(d) | 72.8(d) | 74.5(d) |
| C-5D | 68.1(d) | 62.1(d) | 62.1(d) | 62.4(d) | 62.3(d) | 62.4(d) | 62.4(d) |
| C-6D | 18.4(q) | 18.5(q) | 19.0(q) | 18.4(q) | 18.8(q) | 18.4(q) | 19.8(q) |
| C-1E | 97.1(d) | 97.9(d) | 97.9(d) | 97.9(d) | 97.8(d) | 97.8(d) | 97.8(d) |
| C-2E | 35.7(t) | 32.3(t) | 32.7(t) | 32.3(t) | 32.3(t) | 32.7(t) | 32.6(t) |
| C-3E | 91.0(s) | 72.7(s) | 72.7(s) | 72.7(s) | 72.7(s) | 72.8(s) | 72.7(s) |
| C-4E | 53.8(d) | 55.5(d) | 55.5(d) | 55.4(d) | 55.4(d) | 55.4(d) | 55.4(d) |
| C-5E | 69.1(d) | 67.7(d) | 67.7(d) | 67.7(d) | 67.7(d) | 67.7(d) | 67.7(d) |
| C-6E | 17.0(q) | 17.1(q) | 17.9(q) | 17.0(q) | 17.0(q) | 17.0(q) | 17.0(q) |
| 3E-CH₃ | 25.3(q) | 34.1(q) | 34.1(q) | 34.0(q) | 34.0(q) | 34.1(q) | 34.0(q) |
| 4E-COCH₃ | 157.4(s) | 170.4(s) | 170.4(s) | 170.5(s) | 170.4(s) | 170.4(s) | 170.4(s) |
| 4E-COCH₃ | 52.7(q) | 23.4(s) | 23.5(q) | 23.4(q) | 23.4(q) | 23.4(q) | 23.4(q) |

BIOLOGICAL ACTIVITY

The six antibacterials represented by formula I exhibited in vitro antibacterial activity in a Sabourand dextrose broth medium against 14 Gram positive microorganism. (geometric mean have MICs≈>4 mcg/mL, MHB<pH 7.4 after 24 hrs). The preferred compounds of formula Ia wherein $R_1=CH_3$, $R_2=OH$ and $R_3=$

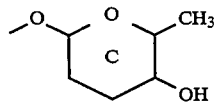

and Ib wherein $R_1=CH_2CH_3$, $R_2=OH$ and $R_3=$

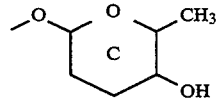

exhibited (a) geometric mean MICs of >2 against the Gram positive organism Sarcina lutea 9341 and (b) in an in vitro anti-chlamydial assay (using McCoy cell cultures infected with Chlamydia trachomatis, Serotype H (VR-879) obtained from the ATCC) showed significant (i.e., >85 and even 100% inhibition of Chlamydia trachomatis serotype H at concentrations 1.0 and 0.5 μg/mL. Neither of these two compounds (Ia, or Ib) showed any cytotoxicity at the concentrations tested.

The other four antibacterials (Ic–If) did not demonstrate notable inhibition of Chlamydia or cytotoxicity at the concentrations tested.

Anti-Chlamydia Test Protocol

Chlamydia trachomatis, serotype H, (VR-879) obtained from the ATCC was propagated in McCoy cells in disposable tissue culture labware at 37° C. in a humidified atmosphere of 5% $CO_2$. Inclusions were visualized following staining using a fluorescein conjugated monoclonal antibody directed against Chlamydia trachomatis specific antigens.

McCoy cell cultures were processed and grown as monolayers on coverslips in 1 dram shell vials. Eagles Minimal Essential Media (E-MEM) supplemented with 10% (v/v) heat inactivated fetal bovine serum (FBS), 5.4 g/L glucose, 2 μg/ml cycloheximide, 2.5 μg/ml fungizone, 2 mM L-glutamine, 10 μgml gentamicin, and 10 mM Hepes was used to maintain test cultures.

EXPERIMENTAL DESIGN

Preparation of Compound for AntiChlamydia Test

Each compound of formula I was diluted iln 100% DMSO. Final dilutions of 1.0, 0.5, 0.1, 0.05, 0.01, and 0.005 μg/ml were prepared in maintenance media. The final concentration of DMSO in each dilution was 1%. The diluted compounds were soluble and prepared on the day of use.

Chlamydia Preparation

Dilutions of C. trachomatis were cultured on McCoy cells, stained using a specific fluorescent antibody, and inclusions quantitated to determine that dilution of organism to be used in the assay.

Test Method

C. trachomatis stock was diluted 1:30 in maintenace media. Media was gently aspirated from each McCoyt culture shell vial and replaced with 100 μl of either Chlamydia (test and Chlamydia control wells) or media (cytotoxicity and cell control wells). The cultures were centrifuged at 4300 RPM for 60 minutes and then incubated at 37° C. for 30 minutes. The cells were gently washed 3 times with media to remove any unadsorbed inoculum. Following the washing, 1 ml of either compound dilution (cytotoxicity and test wells) or media (cell control and Chlamydia control wells) was added to the cell monolayer.

Incubation

The cultures were incubated at 37° C. in humidified air supplemented with 5% $CO_2$ for 48 hours. The cells were monitored by microscopic observations for cytotoxicity.

Assay for Chlamydia Recovery

Following the 48 hours incubation period, final microscopic observations for cytotoxicity were recorded. A fluorescent antibody assay was performed using Syva's fluorescein conjugated monoclonal antibody directed at the Chlamydia trachomatis antigen.

Calculation

% of Chlamydia Control: Test/Chlamydial control×100 Test=Mean number of inclusions in the test cultures Chlamydia control=Mean number of inclusions in the Chlamydia control compounds Ia and Ib exhibited 100% inhibition of Chlamydia infections at 1.0 μg/mL.

Pharmaceutical Compositions

This invention contemplates antibacterially effective pharmacutical compositions comprising an antimicrobially effective amount of a compound of formula I in admixture with a pharmaceutically acceptable, non-toxic carrier adapted for topical, oral or parenteral use.

The topical, oral and parenteral dosage forms may be prepared according to procedures well known in the art, and may contain a variety of ingredients.

In the case of topical formulations, e.g., ointments, creams, lotions, powders, tablets, pessaries or sprays, the formulation will contain about 10 mg to 10 grams of a compound of formula I per 100 grams of carrier and preferably about 100 mg to about 1 gram of a compound of formula I per 100 grams of carrier.

Oral dosage forms include tablets, capsules, elixirs, suspensions, and the like. Tablets contain such excipients as starch or lactose; liquid forms may contain coloring or flavoring agents.

Parenteral forms to be injected intravenously, intramuscularly, or subcutaneously are usually in the form of a sterile solution, and masy contain salts or glucose to make the solution isotonic.

In general, the topical dosage range of the compound of formula I is from about 0.1% to about 10% by weight of a particular pharmaceutical composition formulated in single or divided doses, with the preferred range being about 0.5% to about 4% and with the most preferred range being about 1% to about 2%.

In general, the oral dosage for humans of the compound of formula I administered to combat a given bacterial infection ranges from about 1 mg per kilogram of body weight to about 50 mg per kilogram of body weight per day, in single or divided doses, with about 2 mg per kilogram of body weight to about 20 mg per kilogram of body weight per day being preferred.

In general, the parenteral dosage for humans of the compound of formula I administered to combat a given bacterial infection ranges for about 0.1 mg per kilogram of body weight per day, to about 20 mg per kilogram of body weight per day, in single or divided doses, with about 1 mg per kilogram of body weight per day being preferred.

It will be appreciated that the actual preferred dosages of a compound of this invention will vary according to the particular composition formulated, the mode of application and the particular situs, as well as the health of the host being treated. Many factors that modify the action of the drug will be taken into account by the attending clinician, e.g., age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by the attending clinician using conventional dosage determination tests.

This invention also contemplates anti-chlamydia effective pharmacutical compositions comprising an antichlamydia effective amount of a compound of formula I, e,g., at least one compound of formula 1a wherein $R_1=CH_3$, $R_2=OH$, and $R_3=$

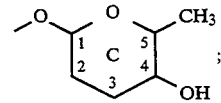

or of formula Ib wherein $R_1=CH_2CH_3$, $R_2=OH$ and $R_3=$

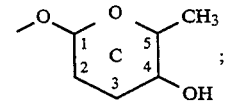

in admixture with a pharmaceutically acceptable, non-toxic carrier adapted for topical, oral or parenteral use. The pharmaceutical composition may also contain a compound of formula Ia or Ib in admixture with one or more of compounds of formula Ic–If.

The topical, oral and parenteral dosage forms may be prepared according to procedures well known in the art, and may contain a variety of ingredients so long as antichlamydia effective amount of a compound of formula Ia or IIa is present; mixtures of Ia or Ib in admixture with one or more of Ic–If may also be used.

In the case of topical formulations for treating and/or preventing Chlamydia infections, e.g., ointments, creams, lotions, powders, tablets, pessaries or sprays, the formulation will contain about 1 mg to 1 gram of an anti-chlamydia compound of formula I per 100 grams of carrier and preferably about 10 mg to about 100 mg of a compound of formula I per 100 grams of carrier.

Oral dosage forms for treating and/or preventing Chlamydia infections include tablets, capsules, elixirs, suspensions, and the like. Tablets contain such excipients as starch or lactose; liquid forms may contain coloring or flavoring agents.

Parenteral forms for treating and/or preventing Chlamydia infections to be injected intravenously, intramuscularly, or subcutaneously are usually in the form of a sterile solution, and may contain salts or glucose to make the solution isotonic.

In general, the topical dosage range for treating and/or preventing Chlamydia infections in humans of an anti-chlamydia compound of formula I is from about 0.01% to about 1% by weight of a particular pharmaceutical composition formulated in single or divided doses, with the preferred range being about 0.05% to about 0.5% and with the most preferred range being about 0.01% to about 0.5%.

In general, the oral dosage for humans of an anti-chlamydia compound of formula I administered to combat a given Chlamydia infection ranges from about 0.1 mg per kilogram of body weight to about 50 mg per kilogram of body weight per day, in single or divided doses, with about 0.2 mg per kilogram of body weight to about 20 mg per kilogram of body weight per day being preferred.

In general, the parenteral dosage for humans of an anti-chlamydia compound of formula I administered to combat a given Chlamydia infection ranges for about 0.01 mg per kilogram of body weight per day, to about 2 mg per kilogram of body weight per day, in single or divided doses, with about 0.5 mg per kilogram of body weight per day being preferred.

It will be appreciated that the actual preferred dosages of an anti-chlamydia compound of this invention will vary according to the particular composition formulated, the mode of application and the particular situs, as well as the the host being treated. Many factors that modify the action of the drug will be taken into account by the attending clinician, e.g., age, body weight, sex, diet, time of administration, rate of excretion, condition of the host, drug combinations, reaction sensitivities and severity of the disease. Administration can be carried out continuously or periodically within the maximum tolerated dose. Optimal application rates for a given set of conditions can be readily ascertained by the attending clinician using conventional dosage determination tests.

What is claimed is:

1. A compound represented by formula I

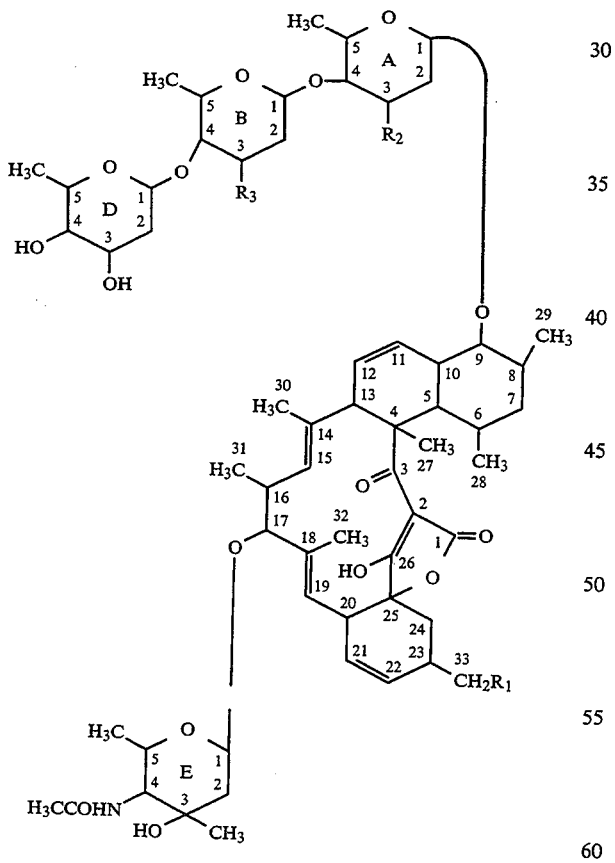

wherein
$R_1=CH_2CH_3$, $R_2=H$, and $R_3=$

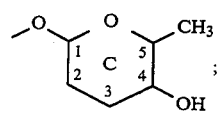

$R_1=CH_3$, $R_2=OH$, and $R_3=$

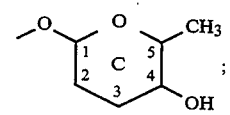

$R_1=CH_2CH_3$, $R_2=OH$, and $R_3=$

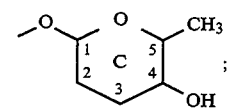

$R_1=Ch_3$, $R_2=H$, and $R_3=OH$;
$R_1=CH_3$, $R_2=H$, and $R_3=$

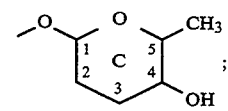

or $R_1=CH_2CH_3$, $R_2=H$, and $R_3=OH$.

2. A compound of claim 1 wherein in formula 1 $R_1=CH_2CH_3$, $R_2=H$ and $R_3=$

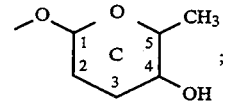

3. A compound of claim 1 wherein in formula 1 $R_1=CH_3$, $R_2=OH$ and $R_3=$

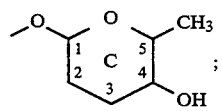

4. A compound of claim 1 wherein in formula 1 $R_1=CH_2CH_3$, $R_2=OH$ and $R_3=$

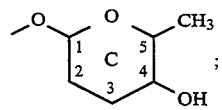

5. A compound of claim 1 wherein in formula 1 $R_1=CH_3$, $R_2=H$ and $R_3=OH$.

6. A compound of claim 1 wherein in formula 1 $R_1=CH_3$, $R_2=H$ and $R_3=$

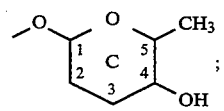

7. A compound of claim 1 wherein in formula 1 $R_1=CH_2CH_3$ and $R_2=H$, $R_3=OH$.

8. A pharmaceutical composition for treating and/or preventing a bacterial infection in mammals which comprises an anti-bacterial effective amount of a compound of claim 1 or mixtures thereof and a pharmaceutically acceptable carrier therefor.

9. The pharmaceutical composition of claim 8 wherein the bacterial infection is a Chlamydia trachomatis infection.

10. A method of treating and/or preventing bacterial infections in a mammal which comprises administering an anti-bacterial effective amount of compound represented by formula I:

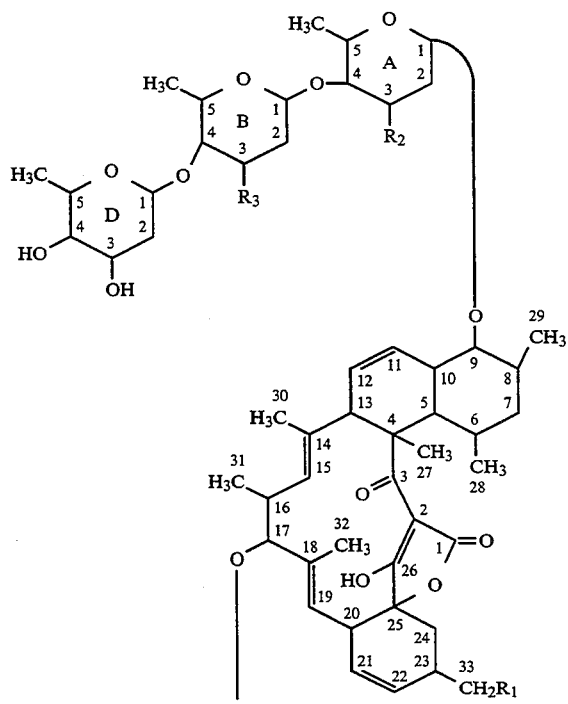

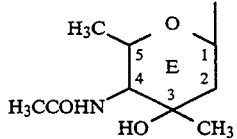

wherein
$R_1=CH_2CH_3$, $R_2=H$, and $R_3=$

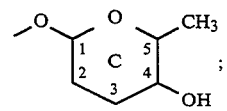

$R_1=CH_3$, $R_2=OH$, and $R_3=$

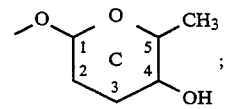

$R_1=CH_2CH_3$, $R_2=OH$, and $R_3=$

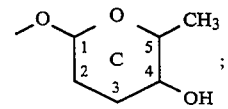

$R_1=CH_3$, $R_2=H$, and $R_3=OH$;
$R_1=CH_3$, $R_2=H$, and $R_3=$

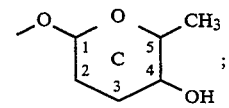

$R_1=CH_2CH_3$, $R_2=H$, and $R_3=OH$;
or mixtures of compounds of formula I or a pharmaceutical composition thereof.

11. A method of claim 10 wherein the bacterial infection is a Chlamydia infection.

12. A method of claim 10 wherein the bacterial Chlamydia infection is caused by Chlamydia trachomatis.

13. A method of claim 10 wherein the bacterial infection is a Chlamydia infection and a compound of formula I wherein $R_1=CH_3$, $R_2=OH$, and $R_3=$

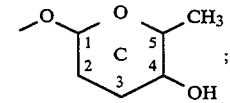

is administered.

14. A method of claim 10 wherein the bacterial infection is a Chlamydia infection and a compound of formula I wherein $R_1=CH_2CH_3$, $R_2=OH$, and $R_3=$

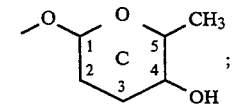

is administered.

15. A method of claim 10 wherein a compound of formula I wherein $R_1=CH_3$, $R_2=H$, and $R_3=OH$ is administered.

16. A method of claim 10 wherein a compound of formula I wherein $R_1=CH_3$, $R_2=H$, and $R_3=$

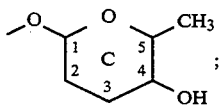

is administered.

17. A method of claim 10 wherein a compound of formula I wherein $R_1=CH_2CH_3$, $R_2=H$, and $R_3=OH$ is administered.

18. A method of claim 10 wherein a compound of formula I wherein $R_1=CH_2CH_3$, $R_2=H$, and $R_3=$

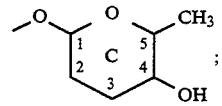

is administered.

19. A method of claim 10 wherein a mixture of the compounds of formula I is used.

* * * * *